United States Patent
Woolfe et al.

(12)

(10) Patent No.: US 6,511,680 B2
(45) Date of Patent: *Jan. 28, 2003

(54) ANTI-INFLAMMATORY PHARMACEUTICAL FORMULATIONS

(75) Inventors: Austen John Woolfe, North Weald (GB); Gordon McIntyre, Bishops Stortford (GB); Nitin Vadilal Sheth, Goshen, NY (US)

(73) Assignee: Norton Healthcare Ltd., Harlow (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/045,406

(22) Filed: Nov. 19, 2001

(65) Prior Publication Data

US 2002/0132004 A1 Sep. 19, 2002

Related U.S. Application Data

(63) Continuation of application No. 09/789,365, filed on Feb. 20, 2001, now Pat. No. 6,319,519, and a continuation of application No. 09/346,122, filed on Jul. 1, 1999, now abandoned.
(60) Provisional application No. 60/091,960, filed on Jul. 7, 1998.

(51) Int. Cl.$^7$ .................................................. A61K 9/24
(52) U.S. Cl. ........................ 424/472; 424/464; 424/465; 424/480; 424/489; 424/490; 424/494; 424/495; 424/497; 424/499
(58) Field of Search ................................. 424/400, 451, 424/463, 464, 468, 472, 474, 489, 490

(56) References Cited

U.S. PATENT DOCUMENTS

| | | |
|---|---|---|
| 6,183,779 B1 | 2/2001 | Ouali et al. |
| 6,287,600 B1 | 9/2001 | Ouali et al. |
| 6,319,519 B2 * | 11/2001 | Woolfe et al. ............... 424/464 |
| 6,387,410 B1 | 5/2002 | Woolfe et al. |
| 6,106,862 A1 | 8/2002 | Chen et al. |

* cited by examiner

Primary Examiner—Thurman K. Page
Assistant Examiner—Charesse Evans
(74) Attorney, Agent, or Firm—Beyer Weaver & Thomas LLP

(57) ABSTRACT

A pharmaceutical dosage form comprising a tablet containing a non-steroidal anti inflammatory drug and misoprostol, wherein the non-steroidal anti inflammatory drug is in the form of coated pellets.

28 Claims, No Drawings

ANTI-INFLAMMATORY PHARMACEUTICAL FORMULATIONS

This application is a con't of Ser. No. 09/789,365 filed Feb. 20, 2001 U.S. Pat. No. 6,319,519 and a con't of Ser. No. 09/346,122 filed Jul. 8, 1999 abandoned and claims benefit of Provisional No. 60/091,960 filed Jul. 7, 1998.

This invention relates to pharmaceutical formulations of anti-inflammatory drugs, particularly non-steroid and anti-inflammatory drugs (NSAIDs).

These NSAIDs are used for the treatment of inflammatory conditions such as osteoarthritis or rheumatoid arthritis. A side effect of the oral administration of NSAIDs particularly with long term usage, is a liability to ulcerogenic effects. NSAID induced ulcers in the stomach are potentially dangerous because few or no symptoms may be detected until significant damage has been caused. Certain prostoglandins, for example misoprostol have been shown to reduce and even prevent such ulcers.

It has been found experimentally that it is necessary for the prostaglandin to be released before the NSAID so as to protect the stomach from the effects of the NSAID. It is therefore preferable that the NSAID is coated to delay release. The coating may be a standard hydroxypropyl methyl cellulose coat of a thickness sufficient to delay release in the stomach for a short period, an enteric coat to delay NSAID release until it reaches the intestine, or a delay release coating to allow drug release over a period of time to permit less frequent dosing.

In addition the coating may act as a barrier between the NSAID and the prostaglandin to prevent decomposition of the prostaglandin caused by instability in the pressure of the NSAID.

EP-527887B discloses a pharmaceutical composition comprising a core of an NSAID surrounded by a coating containing the prostaglandin. The core is preferably coated with a barrier of enteric coat before a mantle coat is added. No experimental details are given. It appears that this dosage form is made by press-coating, ie a tablet core containing the drug is made, and coated before being put in a second tableting operation to cover the coated core. Such a procedure requires use of specialised equipment which is not a normal pharmaceutical production tool and hence would need significant investment.

According to the present invention an oral pharmaceutical dosage form comprises a tablet containing a non-steroidal anti-inflammatory drug and misoprostol, wherein the non-steroidal anti-inflammatory drug is in the form of coated pellets.

The NSAID is preferably but not exclusively one of reasonably low weight per standard dose. That is an NSAID where the usual dose is 200 mg or below. Examples of such NSAIDs include indomethacin, piroxicam, meloxicam, flubiprofen, naproxan, ketoprofen, tenoxicam or similar molecules. Most preferably the drug is diclofenac sodium.

Enteric coated or delay release coated pellets have not been widely used because many workers have found damage or cracking to the enteric or delay release coating during the tablet compression stage. The present invention will work most effectively if the coating remains intact during compression.

It is possible to produce such pellets by conventional means although care is needed to ensure coat cracking does not occur. Techniques which can be used include coating the drug on a non-pariel core preferably composed of inert sugar or similar substance and then overcoating with the required coating before compression.

A preferred method is to form pellets by co-acervation or alternatively by precipitation of the pellets from solution as described by Zaruboru, Fell and Collett, (Int.J.Pharm, 1995, 125, 151–5).

In another preferred technique the pellets may be formed by spheronisation, rotogranulation or a similar technique. Preferably the pellets should be soft enough to deform slightly under compression to avoid cracking but not too soft so as to deform significantly which will also cause cracking or rupture of the coat. A suitable mixture of drug with a suitable amount of an excipient or several excipients can be found by simple, routine experiments. Suitable excipients include polyvinyl pyrolidone, sugars and cellulose derivatives particularly microcrystalline cellulose. A coating for the pellets may employ cellulose derivatives eg hydroxypropyl methyl cellulose, methacrylic acid and derivatives eg methyl methacrylates for example, Eudragrit® (Rhom Pharma), especially Eudragrit L or S. Other standard enteric coating materials for example phthalates, eg cellulose acetate phthalate or preferably hydroxypropylacetate phthalate or polyvinylacetate phthalate. Mixtures of these and other materials may be used to produce delay release coated beads. Normally coating will include plasticisers eg polyethylene glycol, triacilin or phthalate esters.

It has been found in practice that smaller pellets are better for use in accordance with this invention, preferably between 0.25 mm to 1.5 mm in diameter. Most preferably pellets between 0.8 mm to 1.2 mm diameter are employed. Pellets of this diameter show less tendency to crack under the compression forces.

The external compression material will include a prostaglandin, preferably misoprostol together with inert excipients. The prostaglandin may be used neat or it may be preferably diluted on an inert material. A preferred material is misoprostol diluted on hydroxypropyl methyl cellulose or polyvinyl pyrolidone. Other diluents may be used. The other materials which may be employed include inert fillers, binders, lubricants and colorants as used in normal pharmaceutical tablet making. An especially useful material for this invention is microcrystalline cellulose. The dosage of prostaglandin will be chosen to be suitable to prevent or reduce stomach ulceration caused by the NSAID. A suitable dose of misoprostol is between 100–200 micrograms per tablet but this may be increased or decreased depending on the NSAID used.

The coated pellets and prostaglandin mixture are then compressed on conventional tableting equipment. Tablets may have a break line or break lines to facilitate smaller doses. The tablet may be film or sugar coated if required.

Bilayer tablets may be employed. The non-steroidal anti inflammatory drug and excipients may be compressed into the lower half of the tablet and the misoprostol together with excipients superimposed and pressed onto it. A barrier layer may be provided between the two active ingredient-containing layers. The misoprostol containing layer may incorporate excipients to facilitate rapid dissolution of this active ingredient.

The invention is further described by means of example but not in any limitative sense.

EXPERIMENT 1

The following ingredients were employed.

| | | |
|---|---|---|
| | Diclofenac pellets Enteric Coated 40% | 123 mg |
| | Misoprostol Dispersion on HPMC (1:100) | 20 mg |
| 1) | Microcrystaline Cellulose (Avicel 102) | 33 mg |

EXPERIMENT 1-continued

The following ingredients were employed.

| | | |
|---|---|---|
| 2) | Sodium Stored Glycollate | 3 mg |
| 3) | Hydrogenated Cottonseed Oil | 1 mg |

The excipients 1+2 and misoprostol were sieved through a 250 μm screen. The diclofanac pellets were added and blended for 15 min in a cube blender, The lubricant 3) was added and the mixture was reblended for 5 min and compressed at 180 mg/tablet.

EXPERIMENT 2

The mixture from Experiment 1 was blended with the equivalent of another 100 mg of microcrystalline cellulose and was then compressed at 280 mg/tablet.

EXPERIMENT 3

The following ingredients were employed.

| | | |
|---|---|---|
| Mix 1 | Diclofenac Pellets Enteric Coated 40% | 123 mg |
| | Microcrystalline Cellulose | 133 mg |
| | Sodium Starch Glycollate | 3 mg |
| | Hydrogenated Cottonseed Oil | 1 mg |
| Mix 2 | Misoprostol dilution (1:100) | 20 mg |
| | Microcrystalline Cellulose | 196 mg |
| | Sodium Starch Glycollate | 3 mg |
| | Hydrogenated Cottonseed Oil | 1 mg |

Mixture 1 was prepared with sieved excipients and then compressed to form a layer, having a weight of 260 mg. Mixture 2 was prepared and compressed on top of the diclofenac layer to atop weight of 120 mg, ie total 360 mg.

The resulting bilayer tablets were overcoated with an HPMC taste masking coat. The bead diameter was 1.05 to 1.16

Results

Experiment 1 Using USP Baskets

Dissolution in acid 0.1 MHCL for 2 hrs

Less than 4% release.

Dissolution in pH 6.8 Buffer

98–106% release after 1 hr

Scanning Electronic Microscopy showed no breakage of the enteric coating of the pellets after compression.

What is claimed is:

1. A pharmaceutical dosage form comprising a tablet containing a non-steroidal anti inflammatory drug and misoprostol, wherein the non-steroidal anti inflammatory drug is in the form of coated pellets.

2. A dosage form as claimed in claim 1 containing a uniform mixture of coated non-steroidal anti inflammatory pellets and misoprostol.

3. A dosage form as claimed in claim 1 comprising a bilayer tablet containing coated non-steroidal anti inflammatory pellets in one layer and misoprostol in a second layer.

4. A dosage form as claimed in claim 1 wherein the pellets include an overcoating of a barrier layer upon a pellet including a layer of non-steroidal anti inflammatory drugs sprayed or otherwise coated on a non-pariel core.

5. A dosage form as claimed in claim 1 wherein the coating is an enteric coating.

6. A dosage form as claimed in claim 5 wherein the enteric coating is selected from: a methylmethacrylate copolymer, a polyvinylacetate phthalate, cellulose acetate phthalate, or hydroxypropylmethyl cellulose phthalate.

7. A dosage form as claimed in claim 6 wherein the enteric coat includes a plasticiser.

8. A dosage form as claimed in claim 5 including a barrier inert coat disposed between the drug core and the enteric coating.

9. A dosage form as claimed in claim 7 wherein the barrier coat is a cellulose derivative.

10. A dosage form as claimed in claim 1 wherein the pellets are coated with a barrier coat adapted to delay release of the non-asteroidal anti inflammatory drug.

11. A dosage form as claimed in claim 1 wherein the pellets are coated with a delay release coat adapted to release the drug throughout the gastrointestinal tract.

12. A dosage form as claimed in claim 11 wherein the delay release coat is formed from a methacrylate polymer or a mixture of a methacrylate polymer and a cellulose derivative.

13. A dosage form as claimed in claim 1 wherein the pellets have a diameter of 0.25 to 1.5 mm.

14. A dosage form as claimed in claim 13 wherein the pellets have a diameter of 0.8 to 1.2 mm.

15. A dosage form as claimed in claim 1 including one or more excipients selected from binders, lubricants, colorants, bulking agents and disintegrants.

16. A dosage form as claimed in claim 1 wherein the non-steroidal anti inflammatory drug is diclofenac.

17. A dosage foam as claimed in claim 1 wherein the non-steroidal anti inflammatory drug is ketoprofen.

18. A dosage form as claimed in claim 1 wherein the non-steroidal anti inflammatory drug is naproxen.

19. A dosage form as claimed in claim 1 wherein the non-steroidal anti inflammatory drug is selected from piroxicam and meloxicam.

20. A dosage form as claimed in claim 1 comprising a tablet overcoated with a sugar or cellulose film barrier coating.

21. A dosage form as claimed in claim 1 comprising a tablet overcoated with a barrier or taste masking coating.

22. A dosage form as claimed in claim 1 comprising a tablet wherein the ratio of diclofenac to excipients either in the whole tablet or in the diclofenac layer is between 70:30 and 30:70 parts by weight.

23. A method of manufacture of a pharmaceutical dosage form as claimed in claim 1 wherein the pellets are formed by extrusion and spheronisation of a mixture containing a non-steroidal anti inflammatory drug, followed by coating with a barrier coat.

24. A method of manufacture of a dosage form as claimed in claim 1 wherein the pellets are made by coasservation or precipitation from solution.

25. A method as claimed in claim 24 wherein an enteric coat is formed by contacting solutions of an alkali salt of a non-steroidal anti inflammatory drug, and enteric form forming polymer and an acid.

26. A method as claimed in claim 24 wherein the misoprostol is absorbed onto hydroxypropylmethylcellulose or other cellulose derivative prior to incorporation into a tablet.

27. A method of manufacture of a pharmaceutical tablet comprising the steps of mixing a coated pellet containing a non-steroidal anti inflammatory drug together with a powder containing misoprostol absorbed on a cellulose, polyvinylchloride or other excipient optionally together with one or more binding agents, bulking agents, disintegrants and lubricants and compressing the mixture to form tablets.

28. A method of manufacture of a pharmaceutical bilayer tablet consisting of mixing coated pellets containing a non-steroidal anti inflammatory drug with optional excipients selected from binders, bulking agents, disintegrants and lubricants; compressing the mixture to form the bottom half of a tablet and superimposing a mixture of misoprostol absorbed on a cellulose or polyvinylchloride or other material together with or more optional excipients selected from binders, bulking agents, disintegrants and lubricants; to form a tablet suitable for human administration.

* * * * *